(12) United States Patent
Youn et al.

(10) Patent No.: US 11,478,413 B2
(45) Date of Patent: Oct. 25, 2022

(54) METHOD FOR MANUFACTURING BLACK GINSENG LOW MOLECULAR COLLAGEN ESSENCE

(71) Applicant: Agricultural Corporation Gagopa-Healing Food, Changwon-si (KR)

(72) Inventors: Geum Joung Youn, Changwon-si (KR); Yeon Ju Kwak, Changwon-si (KR)

(73) Assignee: Agricultural Corporation Gagopa-Healing Food, Changwon-si (KR)

( * ) Notice: Subject to any disclaimer, the term of this patent is extended or adjusted under 35 U.S.C. 154(b) by 14 days.

(21) Appl. No.: 17/348,925

(22) Filed: Jun. 16, 2021

(65) Prior Publication Data
US 2022/0151905 A1    May 19, 2022

(30) Foreign Application Priority Data

Nov. 18, 2020  (KR) .................. 10-2020-0154970

(51) Int. Cl.
*A61K 36/00*     (2006.01)
*A61K 8/65*      (2006.01)
*A61K 8/9789*    (2017.01)
*A61K 8/9728*    (2017.01)
*A61Q 19/08*     (2006.01)
*A23L 33/105*    (2016.01)
*A23L 33/17*     (2016.01)
*C12P 21/02*     (2006.01)

(52) U.S. Cl.
CPC .............. *A61K 8/65* (2013.01); *A23L 33/105* (2016.08); *A23L 33/17* (2016.08); *A61K 8/9728* (2017.08); *A61K 8/9789* (2017.08); *A61Q 19/08* (2013.01); *C12P 21/02* (2013.01); *A23V 2002/00* (2013.01); *A61K 2800/85* (2013.01); *A61K 2800/92* (2013.01)

(58) Field of Classification Search
CPC ....................................... A61K 8/65
See application file for complete search history.

(56) References Cited

FOREIGN PATENT DOCUMENTS

| KR | 101840213 B1 | 3/2018 |
| KR | 101841461 B1 | 3/2018 |
| KR | 20200060890 A * | 6/2020 |

* cited by examiner

*Primary Examiner* — Qiuwen Mi
(74) *Attorney, Agent, or Firm* — Leepi

(57) ABSTRACT

In a method for manufacturing black ginseng low molecular collagen essence, koji mould is added to ginseng, to manufacture black ginseng. The black ginseng is mixed with oligosaccharide, to manufacture black ginseng concentrate. The black ginseng concentrate is fermented and sterilized after adding collagen to the black ginseng concentrate.

5 Claims, 3 Drawing Sheets

METHOD FOR MANUFACTURING BLACK GINSENG LOW MOLECULAR COLLAGEN ESSENCE

This application claims priority under 35 U.S.C. § 119 to Korean Patent Application No. 10-2020-0154970, filed on Nov. 18, 2020, the disclosure of which is incorporated by reference herein in its entirety.

BACKGROUND

1. Field of Disclosure

The present disclosure of invention relates to a method for manufacturing black ginseng low molecular collagen essence, and more specifically the present disclosure of invention relates to a method for manufacturing black ginseng low molecular collagen essence, capable of making collagen to be low molecular collagen via adding the collagen to black ginseng concentrate for fermentation.

2. Description of Related Technology

Collagen is a fiber protein, and occupies most of all connective tissue inside of a body such as a skin, a cartilage and so on. Thus, recently, using the characteristics of the collagen, various kinds of edible products having the collagen are released, for preventing skin aging or increasing regeneration effect of the skin, the cartilage and so on.

In addition, as the products having the collagen are released, various kinds of technologies treating the collagen have been developed.

For example, Korean patent No. 10-1841461 discloses cosmetic composition with donkey skin extract including low molecular collagen, and Korean patent No. 10-1840213 discloses production method of low molecular collagen peptide and food composition using the low molecular collagen peptide.

Likewise, to increase the absorption of the collagen into the body, the technologies of the method for manufacturing the low molecular collagen or the foods having the low molecular collagen have been developed.

SUMMARY

The present invention is developed to solve the above-mentioned problems of the related arts. The present invention provides a method for manufacturing black ginseng low molecular collagen essence, capable of making collagen to be low molecular collagen via adding the collagen to black ginseng concentrate for fermentation.

According to an example embodiment, in a method for manufacturing black ginseng low molecular collagen essence, koji mould is added to ginseng, to manufacture black ginseng. The black ginseng is mixed with oligosaccharide, to manufacture black ginseng concentrate. The black ginseng concentrate is fermented and sterilized after adding collagen to the black ginseng concentrate.

In an example, in the manufacturing the black ginseng, 0.2 weight % of the koji mould may be added to 99.8 weight % of the ginseng, and then stored with a temperature between about 50° C. and about 60° C. more than one week.

In an example, in the manufacturing the black ginseng concentrate, the black ginseng may be mixed with the oligosaccharide with a weight ratio of 1:2, and then stored with a temperature between about 50° C. and about 60° C. more than one week.

In an example, in the fermenting and sterilizing, 3 weight % of the collagen may be added to 97 weight % of the black ginseng concentrate, and then stored and fermented with a temperature between about 50° C. and about 60° C. during one day to three days, to manufacture black ginseng low molecular collagen essence. The fermented black ginseng low molecular collagen essence may be sterilized with a temperature more than about 90° C. during ten minutes to thirty minutes.

In an example, the collagen included in the black ginseng concentrate may be to be a low molecular collagen by the fermenting.

According to the present example embodiments, the collagen mixed with the black ginseng concentrate is to be low molecular collagen via the fermentation, so that the absorption into the body may be relatively increased. Thus, the effect of the collagen and the absorption of the black ginseng may be more increased.

DETAILED DESCRIPTION

Figure 1:
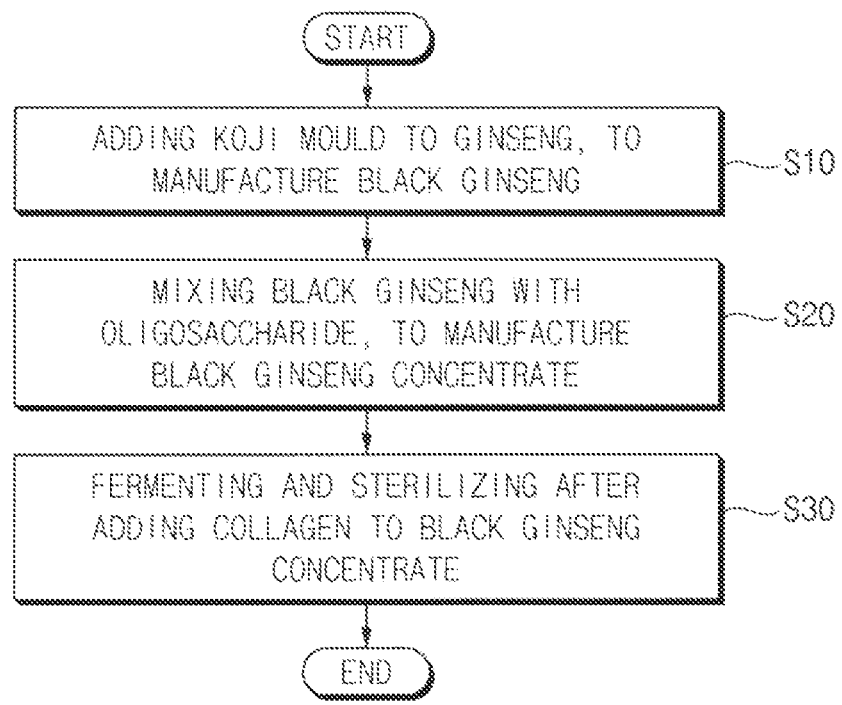
FIG. 1 is a method for manufacturing black ginseng low molecular collagen essence according to an example embodiment of the present invention.

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention is described more fully hereinafter with reference to the accompanying drawings, in which embodiments of the invention are shown.

FIG. 1 is a method for manufacturing black ginseng low molecular collagen essence according to an example embodiment of the present invention.

Referring to FIG. 1, in the method for manufacturing the black ginseng low molecular collagen essence, first, koji mould is added to ginseng, to manufacture black ginseng (step S10).

The ginseng is firstly washed and then has an original shape without cutting. Then, the koji mould (Kojipilz) is added to the ginseng, to manufacture the black ginseng.

Here, 0.2 weight % of the koji mould may be added to 99.8 weight % of the ginseng, to manufacture the black ginseng. The ginseng added with the koji mould may be stored with a temperature between about 50° C. and about 60° C., preferably about 55° C., more than one week.

Due to the relatively long time storage, the ginseng may be manufactured to be the black ginseng, by the koji mould.

Then, the black ginseng is mixed with oligosaccharide, to manufacture black ginseng concentrate (step S20).

Here, the black ginseng may be mixed with the oligosaccharide with a weight ratio of 1:2, to manufacture the black ginseng concentrate. That is, the weight ratio between a weight of the black ginseng and a weight of the oligosaccharide is about 1:2. Then, the mixture of the black ginseng and the oligosaccharide may be stored with a temperature between about 50° C. and about 60° C., preferably about 55° C., more than one week.

Thus, the black ginseng concentrate may be manufactured.

Then, fermentation and sterilization are performed after adding collagen to the black ginseng concentrate (step S30).

Here, 3 weight % of the collagen may be added to 97 weight % of the black ginseng concentrate and then the fermentation may be performed. The fermentation may be performed with a temperature between about 50° C. and about 60° C. during one day to three days, preferably two days.

Due to the above fermentation, the collagen becomes low molecular collagen, and thus the black ginseng low molecular collagen essence.

Then, for sterilizing the manufactured black ginseng low molecular collagen essence, the black ginseng low molecular collagen essence is sterilized with a temperature more than about 90° C. during ten minutes to thirty minutes.

Accordingly, the collagen included in the black ginseng concentrate may become the low molecular collagen, and the black ginseng low molecular collagen essence may be manufactured. Here, the manufactured black ginseng low molecular collagen essence may be sterilized, to form or manufacture edible black ginseng low molecular collagen essence.

Figure 2A:
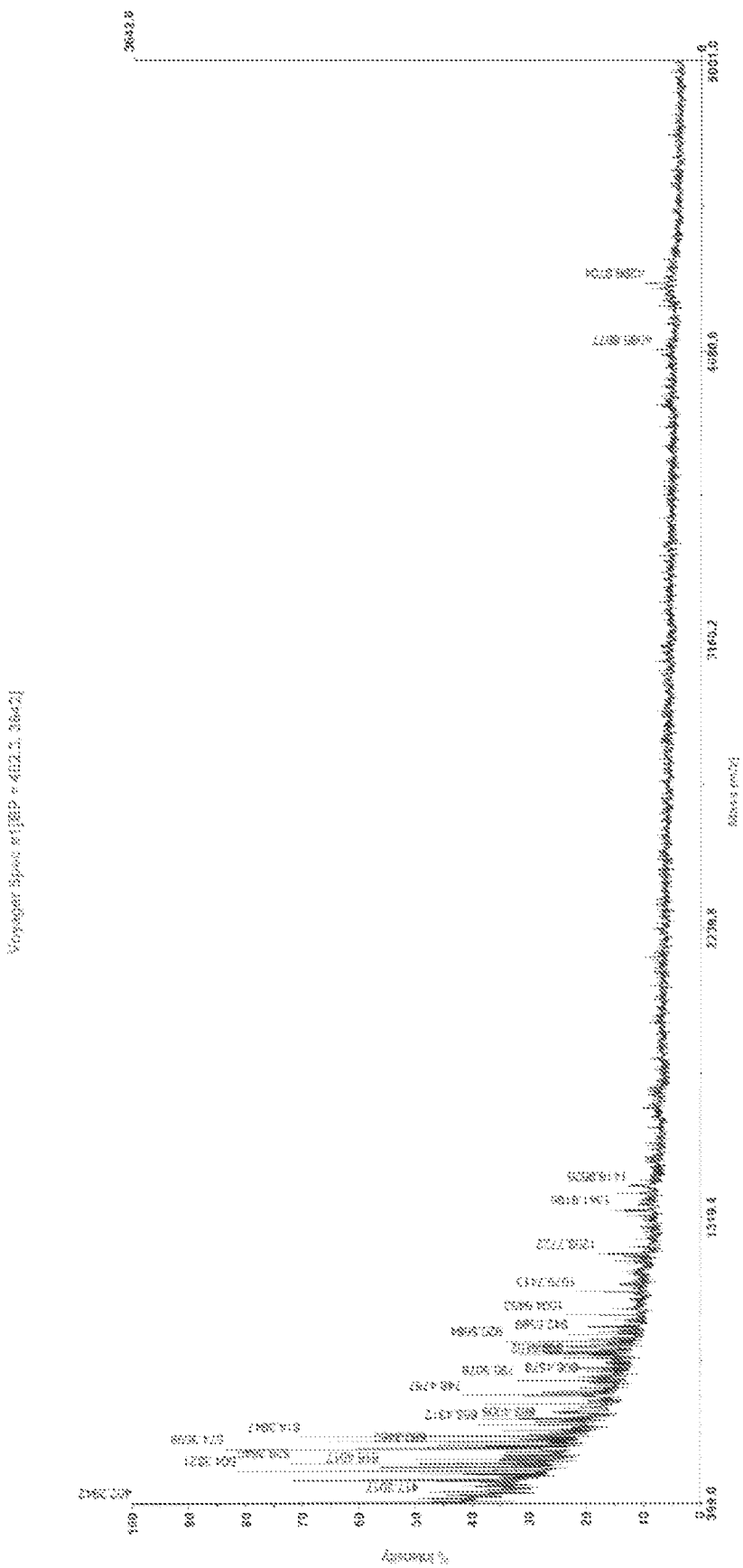
FIG. 2A and FIG. 2B are graphs showing the number of collagen molecules before and after the fermentation, in the method of FIG. 1.
Figure 2B:
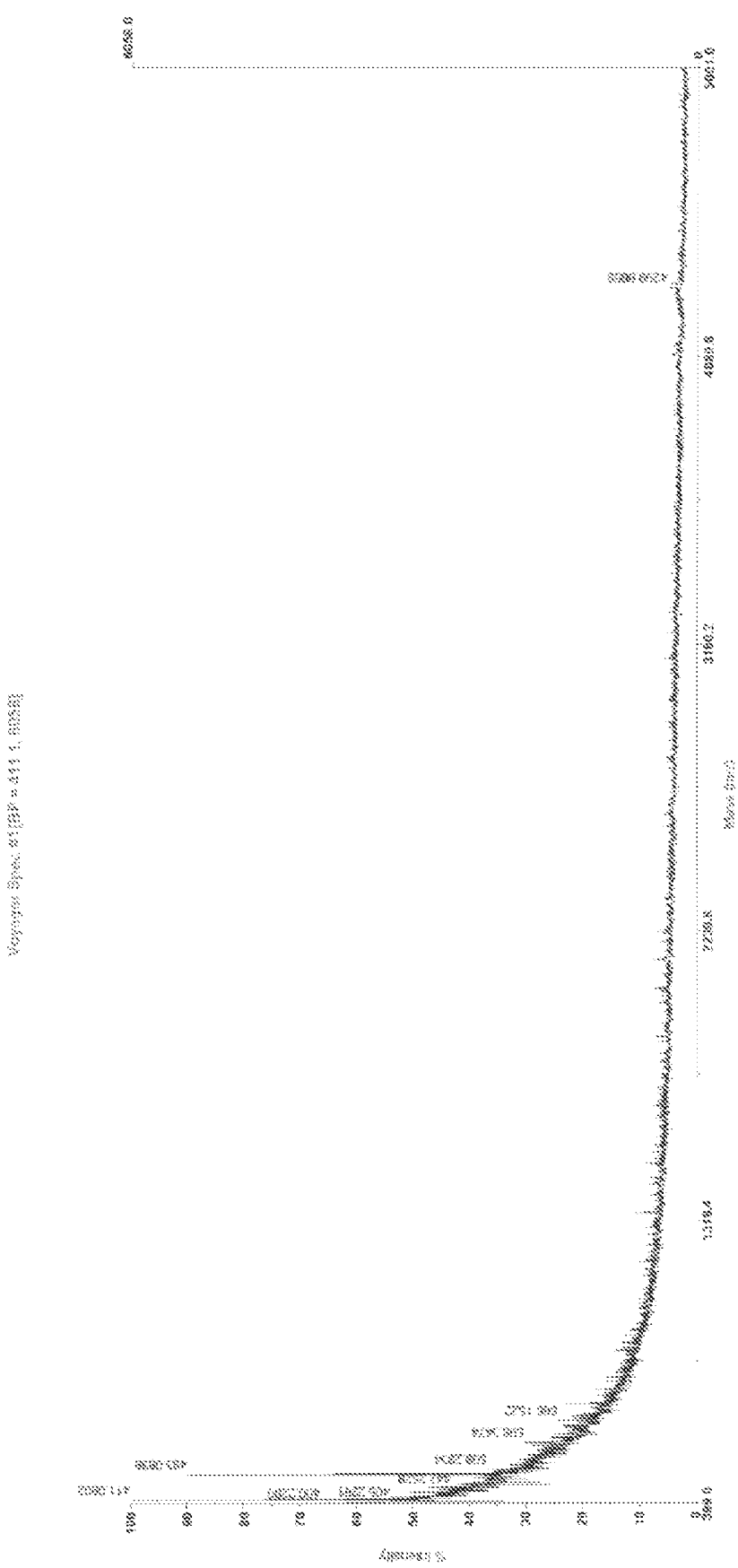

FIG. 2A and FIG. 2B are graphs showing the number of collagen molecules before and after the fermentation, in the method of FIG. 1.

In addition, in cases that the black ginseng low molecular collagen essence is manufactured via the method mentioned above, the number of the low molecular collagens according to the molecular weight before and after the fermentation is listed in Table 1. FIG. 2A and FIG. 2B are graphs showing Table 1.

Referring to Table 1 and FIG. 2A, the kinds of the collagens, that is, the number of the collagens according to the molecular weight are listed, after adding the collagen to the black ginseng concentrate but before the fermentation. In contrast, referring to Table 1 and FIG. 2B, the kinds of the collagens, that is, the number of the collagens according to the molecular weight are listed, after adding the collagen to the black ginseng concentrate and after the fermentation.

TABLE 1

| Number | Molecular weight [da] | Number of collagens | |
|---|---|---|---|
| | | before fermentation | after fermentation |
| 1 | 400~500 | 14 | 229 |
| 2 | 500~600 | 10 | 127 |
| 3 | 600~700 | 11 | 61 |
| 4 | 700~800 | 6 | 1 |
| 5 | 800~900 | 9 | 0 |
| 6 | 900~1,000 | 4 | 0 |
| 7 | 1,000~1,100 | 4 | 0 |
| 8 | 1,100~1,200 | 6 | 0 |
| 9 | 1,200~1,300 | 6 | 0 |
| 10 | 1,300~1,400 | 3 | 0 |
| 11 | 1,400~4,300 | 6 | 1 |
| Total | | 79 | 419 |

As shown in Table 1, FIG. 2A and FIG. 2B, as in the present example embodiment, when the fermentation is performed, the collagen included in the black ginseng concentrate includes a lot of relatively low molecular collagens having the molecular weight between 400 da and 700 da, compared to the collagen before or without the fermentation.

Thus, since the low molecular collagens are more included, when the black ginseng low molecular collagen essence is ingested, the collagen may be more easily absorbed into the body.

According to the present example embodiments, the collagen mixed with the black ginseng concentrate is to be low molecular collagen via the fermentation, so that the absorption into the body may be relatively increased. Thus, the effect of the collagen and the absorption of the black ginseng may be more increased.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A method for manufacturing black ginseng low molecular collagen essence, the method comprising:

adding koji mould to ginseng, to manufacture black ginseng;

mixing the black ginseng with oligosaccharide, to manufacture black ginseng concentrate; and fermenting and sterilizing the black ginseng concentrate, after adding collagen to the black ginseng concentrate.

2. The method of claim 1, in the manufacturing the black ginseng, adding 0.2 weight % of the koji mould to 99.8 weight % of the ginseng, and then storing with a temperature between about 50° C. and about 60° C. for more than one week.

3. The method of claim 1, in the manufacturing the black ginseng concentrate, mixing the black ginseng with the oligosaccharide with a weight ratio of 1:2, and then storing with a temperature between about 50° C. and about 60° C. for more than one week.

4. The method of claim 1, wherein the fermenting and sterilizing comprises:

adding 3 weight % of the collagen to 97 weight % of the black ginseng concentrate, and then storing and fermenting with a temperature between about 50° C. and about 60° C. for one day to three days, to manufacture black ginseng low molecular weight collagen essence; and sterilizing the fermented black ginseng low molecular weight collagen essence with a temperature more than about 90° C. for ten minutes to thirty minutes.

5. The method of claim 1, wherein the collagen included in the black ginseng concentrate is a low molecular weight collagen.

* * * * *